United States Patent
Teasley

(10) Patent No.: US 7,659,026 B2
(45) Date of Patent: Feb. 9, 2010

(54) FLUORINATED SULFONAMIDE COMPOUNDS AND POLYMER ELECTROLYTE MEMBRANES PREPARED THEREFROM FOR USE IN ELECTROCHEMICAL CELLS

(75) Inventor: Mark F. Teasley, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 793 days.

(21) Appl. No.: 10/560,882

(22) PCT Filed: Jun. 25, 2004

(86) PCT No.: PCT/US2004/020703

§ 371 (c)(1),
(2), (4) Date: Dec. 13, 2005

(87) PCT Pub. No.: WO2005/001979

PCT Pub. Date: Jan. 6, 2005

(65) Prior Publication Data

US 2006/0177717 A1    Aug. 10, 2006

(51) Int. Cl.
*H01M 8/10* (2006.01)
*H01M 4/86* (2006.01)
*C08F 8/34* (2006.01)

(52) U.S. Cl. .................................. 429/33; 525/353
(58) Field of Classification Search .............. 429/34
See application file for complete search history.

(56) References Cited

U.S. PATENT DOCUMENTS

| | | |
|---|---|---|
| 3,664,915 A | 5/1972 | Gore |
| 3,953,566 A | 4/1976 | Gore |
| 3,962,153 A | 6/1976 | Gore |
| 4,187,390 A | 2/1980 | Gore |
| 6,090,895 A * | 7/2000 | Mao et al. ............... 525/330.9 |
| 6,264,857 B1 | 7/2001 | Kreuer et al. |
| 6,319,428 B1 | 11/2001 | Michot et al. |

FOREIGN PATENT DOCUMENTS

| | | |
|---|---|---|
| EP | 1 359 142 A1 | 11/2003 |
| WO | WO 03/028145 A2 | 4/2003 |

(Continued)

OTHER PUBLICATIONS

M. Howe-Grant, Fluorine Chemistry: A Comprehensive Treatment, 1995, p. 318, John Wiley, New York (Book Not Included).

(Continued)

*Primary Examiner*—Jerry Lorengo
*Assistant Examiner*—Yun Qian

(57) ABSTRACT

A fluorinated sulfonamide small molecule having the general structure

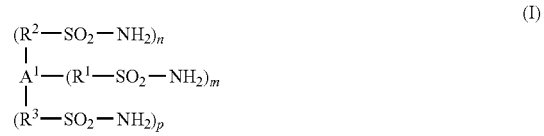

wherein m, n and p are 0 to 3, with the proviso that m+n+p is equal to 1 to 4;
$A^1$ is an aromatic heterocyclic group, with the proviso that carbon atoms of the heterocyclic ring are fully substituted by fluorinated sulfonamide groups; and
$R^1$, $R^2$, and $R^3$ are linear or branched perfluoroalkylene groups, optionally containing oxygen, chlorine, bromine, or iodine atoms. Polymers and small molecules useful in making polymer electrode membranes, membrane electrode assemblies, and electrochemical cells, such as fuel cells, are also described.

31 Claims, 2 Drawing Sheets

FOREIGN PATENT DOCUMENTS

WO     WO 03/034529 A1     4/2003

OTHER PUBLICATIONS

Yoshitsuga Sone et. al., Proton Conductivity of Nafion 117 AS Measured by a Four-Electrode AC Impedance Method, J. Electrochem. Soc., 1996, vol. 143:1254-1259.

Kawahara Kazuo, Solid Polymer Electrolyte for Electrochemical Device and Its Manufacturing method, 2003, vol. 2003, No. 7, Patent Abstracts of Japan (JP 2003 086202 A).

Yong Yu et. al., Study on the Reactions of Fluoroalkanesulfonyl Azides With Pyridine and its derivatives, Tetrahedron, 1999, pp. 13725-13734.

\* cited by examiner

FLUORINATED SULFONAMIDE COMPOUNDS AND POLYMER ELECTROLYTE MEMBRANES PREPARED THEREFROM FOR USE IN ELECTROCHEMICAL CELLS

FIELD OF THE INVENTION

The present invention relates to a novel compound and its use in electrochemical cells as an electrolyte, and more particularly to the use of the compound in polymer electrolyte membranes for fuel cells.

BACKGROUND OF THE INVENTION

Electrochemical cells, such as fuel cells and lithium-ion batteries, are known. Depending on the operating conditions, each type of cell places a particular set of requirements upon the electrolytes used in them. For fuel cells, this is typically dictated by the type of fuel, such as hydrogen or methanol, used to power the cell and the composition of the membrane used to separate the electrodes. Polymer electrolyte membrane fuel cells, powered by hydrogen as the fuel, could be run at higher operating temperatures than currently employed to take advantage of lower purity feed streams, improved electrode kinetics, and better heat transfer from the fuel cell stack to improve its cooling. Waste heat could also be employed in a useful fashion. However, if current fuel cells are to be operated at greater than 100° C. then they must be pressurized to maintain adequate hydration of typical polymer electrolyte membranes, such DuPont Nafibn® perfluorosulfonic acid membrane, to support useful levels of proton conductivity.

There is an ongoing need to discover novel electrolytes that improve the performance of the latest generation of electrochemical cells, such as fuel cells and lithium-ion batteries. For high-temperature fuel cells, this can be addressed by developing new polymer electrolyte membrane materials that maintain adequate proton conductivity at lower levels of hydration.

SUMMARY OF THE INVENTION

In a first aspect, the invention provides a fluorinated sulfonamide small molecule having the general structure:

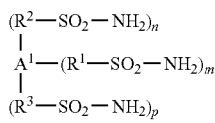
(I)

wherein m, n and p are 0 to 3, with the proviso that m+n+p is equal to 1 to 4;

$A^1$ is an aromatic heterocyclic group, with the proviso that carbon atoms of the heterocyclic ring are fully substituted by fluorinated sulfonamide groups; and $R^1$, $R^2$, and $R^3$ are linear or branched perfluoroalkylene groups, optionally containing oxygen, chlorine, bromine, or iodine atoms.

In a second aspect, the invention provides a polymerizable perfluorinated or partially fluorinated trifluorovinyl monomer that comprises aromatic heterocyclic groups substituted by fluorinated sulfonamide groups, wherein the polymerizable perfluorinated or partially fluorinated trifluorovinyl monomers have the general structure:

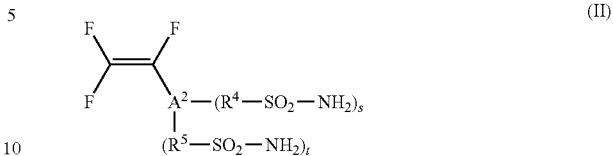
(II)

wherein s and t are the number of fluorinated sulfonamide groups attached to the heterocyclic ring and are equal 0 to 2, with the proviso that s+t is equal to 1 to 2;

$A^2$ is an aromatic heterocyclic group, with the proviso that carbon atoms of the heterocyclic ring are fully substituted by either the trifluorovinyl group or the fluorinated sulfonamide groups; and $R^4$ and $R^5$ are linear or branched perfluoroalkylene groups, optionally containing oxygen, chlorine, bromine, or iodine atoms.

These monomers are useful in the preparation of polymers having general structure (III) shown below.

In a third aspect, the invention provides a fluorinated sulfonamide vinyl polymer having the general structure:

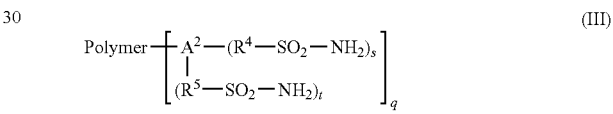
(III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

In a fourth aspect, the invention provides for a polymer electrolyte membrane, typically capable of operating at a temperature of at least 100° C., comprising a compound containing fluorinated sulfonamide groups, —$CF_2$—$SO_2$—$NH_2$, selected from a small molecule having general structure (I), a polymer having general structure (III), and a small molecule having general structure:

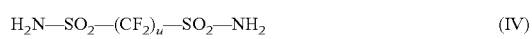
(IV)

wherein u is equal to 1 to 8. By compound is meant a small molecule or a polymer.

In the fourth aspect, the invention further provides a polymer electrolyte membrane comprising a supporting material such as a porous support.

In a fifth aspect, the invention provides a membrane electrode assembly comprising a polymer electrolyte membrane, wherein the polymer electrolyte membrane comprises a compound having fluorinated sulfonamide groups, —$CF_2$—$SO_2$—$NH_2$, selected from the group consisting of:

(a) a small molecule having general structure:

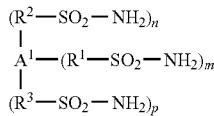 (I)

wherein m, n and p are 0 to 3, with the proviso that m+n+p is equal to 1 to 4;

$A^1$ is an aromatic heterocyclic group, with the proviso that carbon atoms of the heterocyclic ring are fully substituted by fluorinated sulfonamide groups; and $R^1$, $R^2$, and $R^3$ are linear or branched perfluoroalkylene groups, optionally containing oxygen, chlorine, bromine, or iodine atoms;

(b) a polymer having general structure:

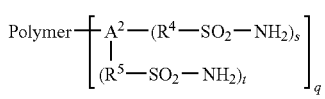 (III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms; and (c) a small molecule having general structure:

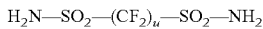 (IV)

wherein u is equal to 1 to 8.

In the fifth aspect, the membrane electrode assembly further comprises at least one electrode prepared from an electrocatalyst coating composition present on the first and second surfaces of the membrane. It also further comprises at least one gas diffusion backing. Alternately, the membrane electrode assembly further comprises a gas diffusion electrode present on the first and second surfaces of the membrane, wherein the gas diffusion electrode comprises a gas diffusion backing and an electrode prepared from an electrocatalyst coating composition.

In a sixth aspect, the invention provides an electrochemical cell, such as a fuel cell, comprising a polymer electrolyte membrane, wherein the polymer electrolyte membrane comprises compounds having fluorinated sulfonamide groups, —$CF_2$—$SO_2$—$NH_2$, selected from a small molecule having general structure (I), a polymer having general structure (III), and a small molecule having general structure (IV).

In the sixth aspect, the fuel cell further comprises an anode or cathode present on the first and second surfaces of the solid polymer electrolyte membrane. Gas diffusion backings may also be present on the anode and cathode on the side away from the polymer electrolyte membrane.

Alternately, in the sixth aspect, the fuel cell comprises gas diffusion electrodes, wherein the gas diffusion electrodes comprise a gas diffusion backing having present thereon an anode or a cathode, and wherein the anode or cathode are adjacent the polymer electrolyte membrane.

In the sixth aspect, the fuel cell further comprises electrocatalyst coatings, wherein a polymer of general structure (III) comprises the binder for the electrocatalyst coatings present as the anode and cathode on a polymer electrolyte membrane or gas diffusion electrodes.

In the sixth aspect, the fuel cell further comprises a means for delivering a fuel to the anode, a means for delivering oxygen to the cathode, a means for connecting the anode and cathode to an external electrical load, a fuel in the liquid or gaseous state in contact with the anode, and oxygen in contact with the cathode. Some suitable fuels include hydrogen; alcohols such as methanol and ethanol; ethers such as diethyl ether, etc. The oxygen can be delivered to the cathode as a pure gas, in a mixture with other inert gases, or as a constituent of air.

In a seventh aspect, the invention provides a binder for electrocatalyst coatings comprising a polymer of general structure (III), wherein the electrocatalyst coatings are present as the anode and cathode on a polymer electrolyte membrane or gas diffusion electrodes in a fuel cell.

DETAILED DESCRIPTION OF THE INVENTION

Figure 1:
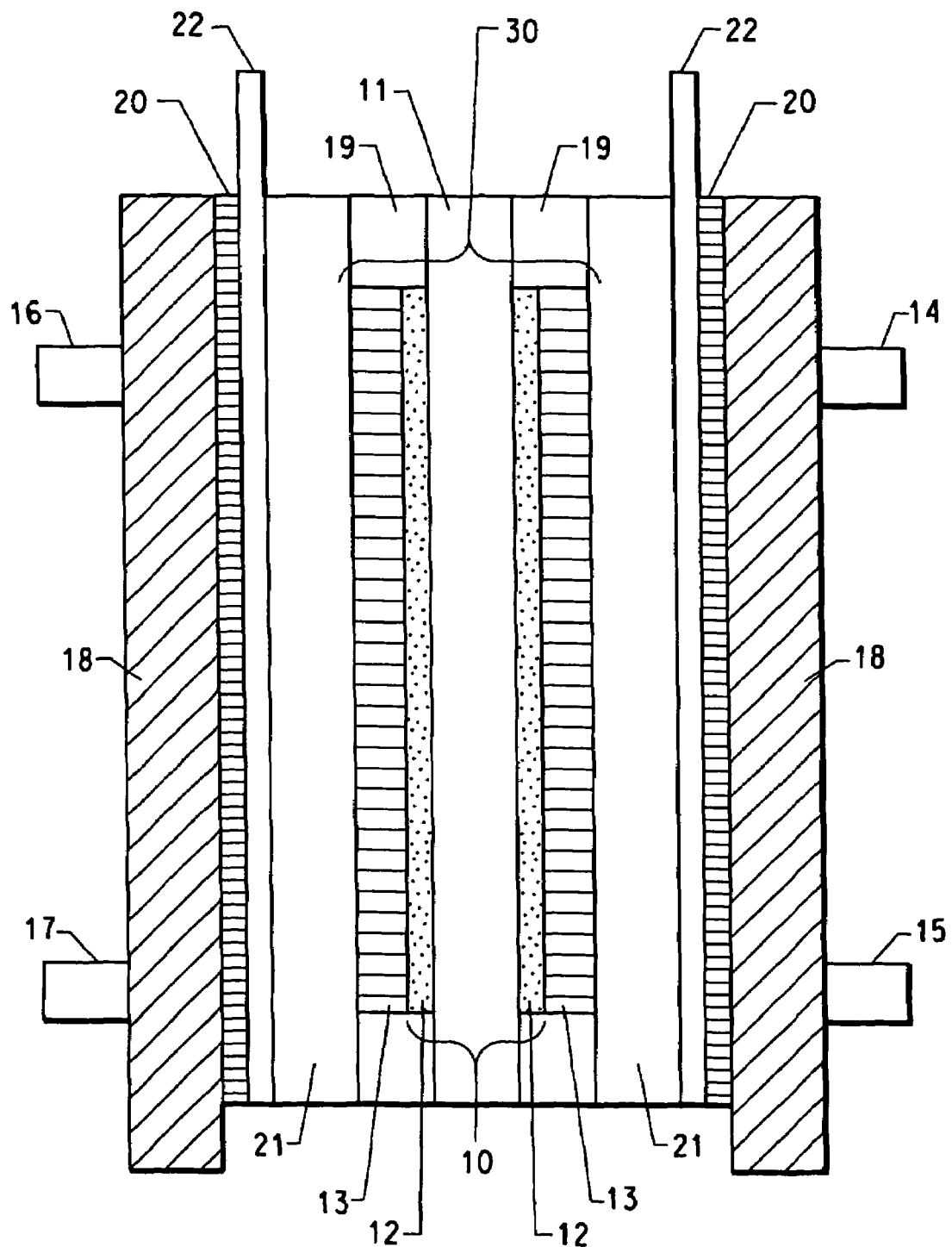
FIG. 1 is a schematic illustration of a single cell assembly.

The ionic or proton-conducting small molecules and polymers of the invention are useful in fuel cells, batteries, chloralkali cells, electrolysis cells, ion exchange membranes, sensors, electrochemical capacitors, and modified electrodes. The monomers of the invention are used for making these useful polymers. These polymers may be used as electrolytes in the preparation of polymer electrolyte membranes and electrocatalyst coating compositions that may be used in the preparation of catalyst coated membranes, gas diffusion electrodes, or membrane electrode assemblies that may be components of an electrochemical cell, such as a fuel cell.

Fluorinated Sulfonamide Small Molecule:

The fluorinated sulfonamide small molecule has the general structure:

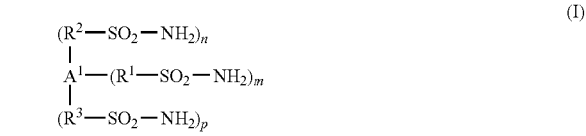 (I)

wherein m, n and p are 0 to 3, typically 1 to 2, with the proviso that m+n+p is equal to 1 to 4, typically 1 to 2; $A^1$ is an aromatic heterocyclic group, such as benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, tetrazoleg, pyrazole, triazole, oxadiazole, or thiadiazole, typically benzimidazole, benzoxazole, benzothiazole, or triazine, and more typically benzimidazole, with the proviso that the carbon atoms of the heterocyclic ring are fully substituted by fluorinated sulfonamide groups; and $R^1$, $R^2$, and $R^3$ are linear or branched perfluoroalkylene groups, optionally containing oxygen, chlorine, bromine, or iodine atoms, typically containing 1 to 20 carbon atoms, and more typically are linear perfluoroalkylene groups containing 1 to 6 carbon atoms.

The fluorinated sulfonamides of the invention may be synthesized by the reaction of fluorinated sulfonyl fluorides or fluorinated sulfonyl anhydrides with ammonia. Various fluorinated bis- and mono-sulfonyl fluorides and anhydrides are known in literature or can be made from fluorinated sulfonic acids (Fluorine Chemistry: A comprehensive treatment, Ed. by M. Howe-Grant John Wiley, New York, 1995, P318). More complicated fluorinated sulfonamides, such as those containing aromatic heterocyclic groups, may also be made from suitable precursors, such as fluorinated sulfonyl fluorides containing acyl fluoride, acyl chloride, or nitrile groups, by reaction with organic reagents, such as ortho-phenylene diamine, ortho-aminophenol, 3,3'-diaminobenzidine, or hydrazine, and cyclization of the heterocyclic ring followed by condensation of the fluorosulfonyl groups with ammonia. The order of the reactions may be reversed if needed due to the reactivity of the organic reagents.

Monomers:

The polymerizable perfluorinated or partially fluorinated trifluorovinyl monomers that comprise aromatic heterocyclic groups substituted by fluorinated sulfonamides have the general structure:

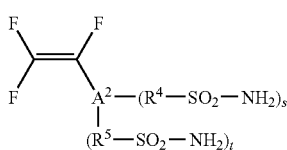

(II)

wherein s and t are the number of fluorinated sulfonamide groups attached to the heterocyclic ring and are equal 0 to 2, with the proviso that s+t is equal to 1 to 2, typically 1; $A^2$ is an aromatic heterocyclic group, such as benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, pyrazole, triazole, oxadiazole, or thiadiazole, typically benzimidazole, benzoxazole, benzothiazole, or triazine, and more typically benzimidazole, with the proviso that carbon atoms of the heterocyclic ring are fully substituted by the trifluorovinyl group or the fluorinated sulfonamide groups; and $R^4$ and $R^5$ are linear or branched perfluoroalkylene groups, optionally containing oxygen, chlorine, bromine, or iodine atoms, typically containing 1 to 20 carbon atoms, and more typically are linear perfluoroalkylene groups containing 1 to 6 carbon atoms.

These monomers are useful in the preparation of polymers having general structure (III) shown below.

Fluorinated Sulfonamide Polymers:

The fluorinated sulfonamide vinyl polymers have the general structure:

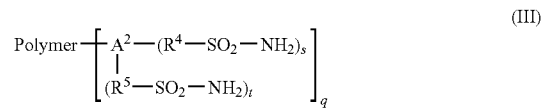

(III)

wherein Polymer is a polyperfluorocarbon or polypartially fluorinated carbon vinyl polymer backbone optionally containing aromatic side chain groups, such as phenyl; q is the mole fraction of fluorinated sulfonamide side chain groups and is selected from 0.01 to 1, typically 0.1 to 1, more typically 0.6 to 1; s and t are the number of fluorinated sulfonamide groups attached to the heterocyclic ring and are equal 0 to 2, with the proviso that s+t is equal to 1 to 2; $A^2$ is an aromatic heterocyclic group, such as benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, pyrazole, triazole, oxadiazole, or thiadiazole, typically benzimidazole, benzoxazole, benzothiazole, or triazine, and more typically benzimidazole, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

There are two basic routes to make fluorinated polymeric sulfonamides:

(a) Fluorinated polymeric sulfonyl fluorides are directly converted to sulfonamide by reaction with ammonia. This can be accomplished on polymer electrolyte membranes or on the polymer resins used for their fabrication. The polymer electrolyte membranes and polymer resins can be exposed to ammonia as a gas, liquid, or solution in suitable solvent. Such solvents may swell the polymer electrolyte membranes and polymer resins without dissolving them, or may dissolve the polymer resins if the resulting solutions of the fluorinated polymeric sulfonamides are to be used for the preparation of polymer electrolyte membranes.

(b) Polymerization of polymerizable monomers containing fluorinated sulfonamide groups. Vinyl monomers containing fluorinated sulfonamide groups may be polymerized in solution, emulsion, or bulk phase using radical initiators, such as potassium persulfate or ammonium persulfate. For example, monomers of general structure (II) may be polymerized alone or with suitable comonomers, such trifluorostyrene or suitable derivatives, to prepare polymers of general structure (III).

Polymer Electrolyte Membrane:

The small molecule of general structure (I) and polymer of general structure (III) can be used as electrolytes to fabricate polymer electrolyte membranes that capable of operation at higher temperatures than typical polymer electrolyte membranes, such Nafion® perfluorosulfonic acid membrane. In addition to these compounds, polymer electrolyte membranes can also be fabricated using the small molecule of general structure:

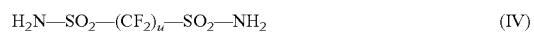

(IV)

wherein u is equal to 1 to 8, typically 2 to 6. Typically, the compounds of general structures (I), (III), and (IV) have an equivalent weight below 300, more typically below 200.

If the small molecule of general structure (I), polymer of general structure (III), or small molecule of general structure (IV) does not have sufficient mechanical strength to make useful polymer electrolyte membranes, supporting materials are needed to make polymer electrolyte membranes from these compounds. The supporting materials may be porous supports as discussed below or the polymers or inorganic materials used in their preparation. The following processes to make membranes are disclosed.

Co-casting: A small molecule or polymer of general structures (I) or (III) is first dissolved in a suitable solvent with supporting polymers, and then co-cast to thin films. After removal of solvent, a membrane is obtained.

Thermal press: If the supporting polymers or materials are not soluble in solvents, thermal pressing may be applied to make membranes. A mixture of a small molecule or polymer of general structure (I) or (III) and supporting polymers or materials are ground or milled first and then thermally pressed into thin films.

Dip coating: A small molecule or polymer of general structure (I) or (III) is dissolved in a suitable solvent. Porous supports such as those discussed below are dipped into the solution and dried repeatedly until the coating is sufficient to give impervious membranes. Inorganic paper and films may also be used for supporting membranes in the dip coating process.

Typically these polymer electrolyte membranes are capable of operating at a temperature of at least 100° C. and a relative humidity of less than 75%, more typically less than 50%, while maintaining a proton conductivity of at least 5 mS/cm, more typically of at least 10 mS/cm at a temperature of at least 150° C. and a relative humidity of less than 25%.

Porous Support:

The porous support of the polymer electrolyte membrane may be made from a wide range of components. The porous support of the present invention may be made from a fluorinated polymer such as polychlorotrifluoroethylene, polytetrafluoroethylene, polyethylene-co-tetrafluoroethylene, and polyvinylidene difluoride, a ceramic such as silica, alumina, and silicon carbide, or a glass such as borosilicate glass. For resistance to thermal and chemical degradation, the porous polymer support typically is made of a highly fluorinated polymer, most typically a perfluorinated polymer.

For example, the polymer for the porous support can be a microporous film of polytetrafluoroethylene (PTFE) or a copolymer of tetrafluoroethylene with other perfluorinated olefins or with perfluorovinyl ethers. Microporous PTFE films and sheeting are known which are suitable for use as a support layer. For example, U.S. Pat. No. 3,664,915 discloses uniaxially stretched film having at least 40% voids. U.S. Pat. Nos. 3,953,566, 3,962,153 and 4,187,390 disclose porous PTFE films having at least 70% voids.

Alternatively, the porous support may be made from fibers of the support materials discussed above by forming the fibers into a paper or a fabric woven using various weaves such as the plain weave, basket weave, leno weave, or others. A membrane suitable for the practice of the invention can be made by coating the porous support paper or fabric with the compound of the invention to form a composite membrane. To be effective the coating must be on both the outside surfaces as well as distributed through the internal pores of the support. This may be accomplished by impregnating the porous support with a solution or dispersion of the polymer suitable for the practice of the invention using a solvent that is not harmful to the polymer or the support, and under impregnation conditions that can form a thin, even coating of the polymer on the support. The support with the solution/dispersion is dried to form the membrane. If desired, thin films of a polymer electrolyte can be laminated to one or both sides of the impregnated porous support to prevent bulk flow through the membrane that can occur if large pores remain in the membrane after impregnation.

It is preferred for the compound to be present as a continuous phase within the solid polymer electrolyte membrane.

Other forms of the solid polymer electrolyte membrane include the PTFE yarn embedded type and the PTFE fibril dispersed type, wherein the PTFE fibril is dispersed in the polymer electrolyte as disclosed in 2000 Fuel Cell Seminar (10/30 to 11/2, 2000, Portland, Oreg.) Abstracts, page 23.

The compounds imbibed into the porous support to form the solid polymer electrolyte membrane may contain reactive functional groups, either as side chains or end groups, that can be used to provide crosslinking, grafting, or chain extension of the polymer to insure that the polymer stays within the porous support and cannot be leached out when in use in a fuel cell. Suitable reactive functional groups include vinyl, trifluorovinyl ether, trifluorovinyl phenyl ether, trifluorovinylbenzene ($\alpha,\beta,\beta$-trifluorostyrene), pentafluorophenyl ether, perfluorinated nitrile perfluorinated bromides, perfluorinated iodides, and alkoxysilanes.

Electrochemical Cell:

As shown in FIG. 1, the electrochemical cell, such as a fuel cell, comprises a catalyst coated membrane (CCM) (10) in combination with at least one gas diffusion backing (GDB) (13) to form an unconsolidated membrane electrode assembly (MEA). The catalyst coated membrane (10) comprises a polymer electrolyte membrane (11) discussed above and catalyst layers or electrodes (12) formed from an electrocatalyst coating composition. The fuel cell is further provided with an inlet (14) for fuel, such as hydrogen; liquid or gaseous alcohols, e.g. methanol and ethanol; or ethers, e.g. diethyl ether, etc., an anode outlet (15), a cathode gas inlet (16), a cathode gas outlet (17), aluminum end blocks (18) tied together with tie rods (not shown), a gasket for sealing (19), an electrically insulating layer (20), graphite current collector blocks with flow fields for gas distribution (21), and gold plated current collectors (22).

Alternately, gas diffusion electrodes (GDE) comprising a gas diffusion backing having a layer of an electrocatalyst coating composition thereon may be brought into contact with a solid polymer electrolyte membrane to form the MEA.

The electrocatalyst coating compositions used to apply the catalyst layers as electrodes on the CCM (10) or the GDE comprises a combination of catalysts and binders dispersed in suitable solvents for the binders, and may include other materials to improve electrical conductivity, adhesion, and durability. The catalysts may be unsupported or supported, typically on carbon, and may differ in composition depending on their use as anodes or cathodes. The binders typically consist of the same polymer used to form the polymer electrolyte membrane (11), but may contain in part as an additive or be solely composed of other suitable polymer electrolytes as needed to improve the operation of the fuel cell. The compounds of this invention may be used either singly or together in the binders or polymer electrolyte membrane (11) with other suitable polymer electrolytes, such as Nafion® perfluorosulfonic acid and sulfonated polyether sulfones, or their membranes.

The fuel cell utilizes a fuel source that may be in the gas or liquid phase, and may comprise hydrogen, an alcohol, or an ether. The fuel is humidified to the degree required to maintain adequate ionic conductivity in the solid polymer electrolyte membrane discussed above so that the fuel cell provides a high power output. Depending on the operating temperature, the fuel cell may be operated at elevated pressures to maintain the required degree of humidification. Typically a gaseous humidified hydrogen feed or methanol/water solution is supplied to the anode compartment, and air or oxygen supplied to the cathode compartment.

Catalyst Coated Membrane (CCM):

A variety of techniques are known for CCM manufacture, which apply an electrocatalyst coating composition similar to that described above onto a solid polymer electrolyte membrane. Some known methods include spraying, painting, patch coating and screen, decal, pad or flexographic printing.

In one embodiment of the invention, the MEA (30), shown in FIG. 1, may be prepared by thermally consolidating the gas diffusion backing (GDB) with a CCM at a temperature of under 200° C., preferably 140-160° C. The CCM may be made of any type known in the art. In this embodiment, an MEA comprises a solid polymer electrolyte (SPE) membrane with a thin catalyst-binder layer disposed thereon. The catalyst may be supported (typically on carbon) or unsupported. In one method of preparation, a catalyst film is prepared as a decal by spreading the electrocatalyst coating composition on a flat release substrate such as Kapton® polyimide film (available from the DuPont Company). After the coating dries, the decal is transferred to the surface of the SPE membrane by the application of pressure and heat, followed by removal of the release substrate to form a catalyst coated membrane (CCM) with a catalyst layer having a controlled thickness and catalyst distribution. Alternatively, the catalyst layer is applied directly to the membrane, such as by printing, and then the catalyst film is dried at a temperature not greater than 200° C.

The CCM, thus formed, is then combined with a GDB to form the MEA (30). The MEA is formed, by layering the CCM and the GDB, followed by consolidating the entire structure in a single step by heating to a temperature no greater than 200° C., preferably in the range of 140-160° C., and applying pressure. Both sides of the MEA can be formed in the same manner and simultaneously. Also, the composition of the catalyst layer and GDB could be different on opposite sides of the membrane.

The invention is illustrated in the following examples.

EXAMPLES

Liquid Conductivity Measurement

The conductivity of a liquid is measured using a cell capable of handling corrosive samples at elevated temperature with volumes as small as 800 µL. Two coil electrodes are formed 25 mm apart by wrapping 0.38 mm diameter platinum wires five times around one end of a 5.14 mm diameter Macor® machinable glass ceramic rod (Corning Inc., Corning, N.Y.) and insulating the remainder of the wire leads with heat-shrink PTFE tubing. The sample is loaded into a 9 mm outside diameter×6.8 mm inside diameter×178 mm length glass tube and the rod is inserted so that the electrodes are completely immersed in the sample. The tube is placed into a forced-convection thermostated oven for heating. The real part of the AC impedance, $R_s$, is measured at a frequency of 1 kHz using a potentiostat/frequency response analyzer (PC4/750™ with EIS software, Gamry Instruments, Warminster, Pa.). The phase angles are typically less than 2 degrees, which indicates that the measurement is unaffected by capacitive contributions from the electrode interfaces. The cell constant, K, is determined by measuring the real part of the impedance, $R_c$, at a frequency of 10 kHz using a NIST traceable potassium chloride conductivity calibration standard for nominal 0.1 S/cm (0.1027 S/cm actual) and calculating as $$K=R_c \times 0.1027 \text{ S/cm} \times (1+\Delta T \times 0.02° \text{ C.}^{-1})$$

where ΔT is the difference between the temperature of the calibration standard, $T_m$, and 25° C. ($\Delta T=T_m-25$). The cell constant is typically close to 12 cm$^{-1}$. The conductivity, κ, of the sample is then calculated as $$\kappa = K/R_s$$

Through-Plane Conductivity Measurement

The through-plane conductivity of a membrane is measured by a technique in which the current flows perpendicular to the plane of the membrane. The lower electrode is formed from a 12.7 mm diameter stainless steel rod and the upper electrode is formed from a 6.35 mm diameter stainless steel rod. The rods are cut to length, and their ends are polished and plated with gold. A stack is formed consisting of lower electrode/GDE/membrane/GDE/upper electrode. The GDE (gas diffusion electrode) is a catalyzed ELAT® (E-TEK Division, De Nora North America, Inc., Somerset, N.J.) comprising a carbon cloth with microporous layer, platinum catalyst, and 0.6-0.8 mg/cm$^2$ Nafion® application over the catalyst layer. The lower GDE is punched out as a 9.5 mm diameter disk, while the membrane and the upper GDE are punched out as 6.35 mm diameter disks to match the upper electrode. The stack is assembled and held in place within a block of Macor® machinable glass ceramic (Corning Inc., Corning, N.Y.) that has a 12.7 mm diameter hole drilled into the bottom of the block to accept the lower electrode and a concentric 6.4 mm diameter hole drilled into the top of the block to accept the upper electrode. A force of 270 N is applied to the stack by means of a clamp and calibrated spring. This produces a pressure of 8.6 MPa in the active area under the upper electrode, which insures a low impedance ionic contact between the GDE's and the membrane. The fixture is placed in a forced-convection thermostated oven for heating. The real part of the AC impedance of the fixture containing the membrane, $R_s$, is measured at a frequency of 100 kHz using a potentiostat/frequency response analyzer (PC4/750™ with EIS software, Gamry Instruments, Warminster, Pa.). The fixture short, $R_f$, is also determined by measuring the real part of the AC impedance at 100 kHz for the fixture and stack assembled without a membrane sample. The conductivity, κ, of the membrane is then calculated as $$\kappa = t/((R_s-R_f) \times 0.317 \text{ cm}^2),$$

where t is the thickness of the membrane in cm.

In-Plane Conductivity Measurement

Figure 2:
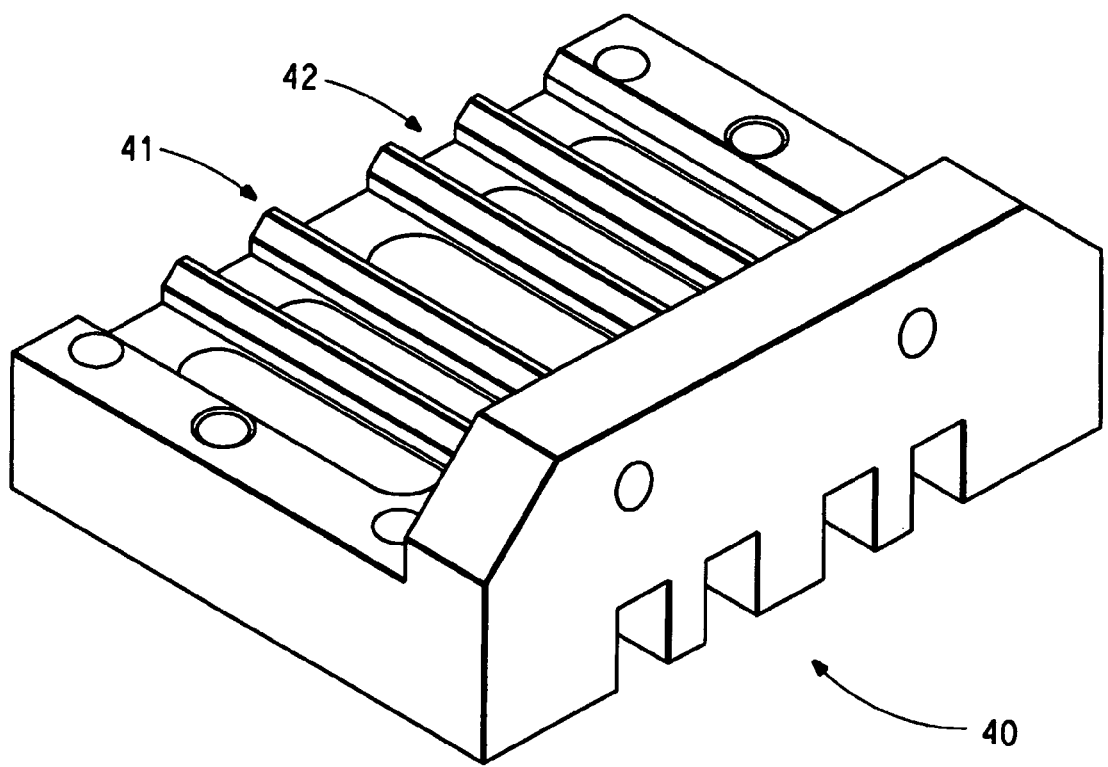
FIG. 2 is a schematic illustration of the lower fixture of a four-electrode cell for in-plane conductivity measurement.

The in-plane conductivity of a membrane is measured under conditions of controlled relative humidity and temperature by a technique in which the current flows parallel to the plane of the membrane. A four-electrode technique is used similar to that described in an article entitled "Proton Conductivity of Nafion® 117 As Measured by a Four-Electrode AC Impedance Method" by Y. Sone et al., J. Electrochem. Soc., 143, 1254 (1996), which is herein incorporated by reference. Referring to FIG. 2, a lower fixture (40) is machined from annealed glass-fiber reinforced PEEK to have four parallel ridges (41) containing grooves that support and hold four 0.25 mm diameter platinum wire electrodes. The distance between the two outer electrodes is 25 mm, while the distance between the two inner electrodes is 10 mm. A strip of membrane is cut to a width between 10 and 15 mm and a length sufficient to cover and extend slightly beyond the outer electrodes, and placed on top of the platinum electrodes. An upper fixture (not shown), which has ridges corresponding in position to those of the bottom fixture, is placed on top and the two fixtures are clamped together so as to push the membrane into contact with the platinum electrodes. The fixture containing the membrane is placed in a small pressure vessel (pressure filter housing), which is placed in a forced-convection thermostated oven for heating. The temperature within the vessel is measured by means of a thermocouple. Water is fed from a calibrated Waters 515 HPLC pump (Waters Corporation, Milford, Mass.) and combined with dry air fed from a calibrated mass flow controller (200 sccm maximum) to evaporate the water within a coil of 1.6 mm diameter stainless steel tubing inside the oven. The resulting humidified air is fed into the inlet of the pressure vessel. The total pressure within the vessel (100 to 345 kPa) is adjusted by means of a pressure-control let-down valve on the outlet and measured using a capacitance manometer (Model 280E, Setra Systems, Inc., Boxborough, Mass.). The relative humidity is calculated assuming ideal gas behavior using tables of the vapor pressure of liquid water as a function of temperature, the gas composition from the two flow rates, the vessel temperature, and the total pressure. Referring to FIG. 2, the slots (42) in the lower and upper parts of the fixture allow access of humidified air to the membrane for rapid equilibration with water vapor. Current is applied between the outer two electrodes while the resultant voltage is measured between the inner two electrodes. The real part of the AC impedance (resistance) between the inner two electrodes, R, is measured at a frequency of 1 kHz using a potentiostat/frequency response analyzer (PC4/750™ with EIS software, Gamry Instruments, Warminster, Pa.). The conductivity, κ, of the membrane is then calculated as κ=1.00 cm/($R \times t \times w$), where t is the thickness of the membrane and w is its width (both in cm).

Example 1

Octafluoro-1,4-butanedisulfonamide, $H_2NSO_2(CF_2)_4SO_2NH_2$, was prepared using the following procedure:

A mixture of 35 g of (77 mmol) of $I(CF_2)_4I$, 33.5 g (192 mmol) of $Na_2S_2O_4$ and 16 g (192 mmol) of $NaHCO_3$ in 300 mL of 1 to 1 water and acetonitrile was stirred under $N_2$ at room temperature for 4 hrs. After removal of volatiles, the residue was dissolved in 100 mL of water and cooled to −10° C. (salt ice bath). Excess $Cl_2$ was slowly added to the solution at below 0° C. and then filtered to give solids, which were redissolved in $CH_2Cl_2$. The $CH_2Cl_2$ solution was washed with water and dried over $MgSO_4$. After removal of $CH_2Cl_2$, 22 g (71.6%) of $ClSO_2(CF_2)_4SO_2Cl$ were obtained. $^{19}F$ NMR: −104.7 (2F), −119.2 (2F).

A mixture of 72.4 g (0.181 mol) of $ClSO_2(CF_2)_4SO_2Cl$ and 30 g (0.516 mol) in 300 mL of acetonitrile was stirred at 70° C. for 26 hrs and filtered. The filtrate was poured into water and the lower layer was separated, washed with water and distilled from $P_2O_5$ to give 36.1 g of $FSO_2(CF_2)_4SO_2F$, bp 90-91° C./200 mmHg. $^{19}F$ NMR: +46.2 (2F), −108.5 (4F), −120.5 (4F).

A solution of 10 g of (27.3 mmol) of $FSO_2(CF_2)_4SO_2F$ in 50 mL of acetonitrile was condensed with excess $NH_3$ gas through a dry ice condenser at room temperature and the resulting mixture was stirred at room temperature overnight. $^{19}F$ NMR indicated that the reaction was complete. After removal of volatiles, the residue was diluted with 80 mL of ether, washed with 5% HCl, water, and dried over $MgSO_4$. After removal of the ether, 9.5 g of a soft white solid were obtained. The solid was sublimed under vacuum. $^{19}F$ NMR: −112.1 (s, 4F), −124.4 (s, 4F).

Example 2

A glass tube was charged with octafluoro-1,4-butanedisulfonamide and analyzed for liquid conductivity. The measurements are shown in Table 1.

TABLE 1

| | Temperature, ° C. | | | | | | |
|---|---|---|---|---|---|---|---|
| | 100 | 125 | 150 | 180 | 150 | 125 | 100 |
| Conductivity, mS/cm | 4.23 | 7.14 | 10.94 | 16.38 | 18.26 | 14.74 | 10.79 |

Example 3

A membrane was prepared using the following procedure:

0.4 g of Nafion® (EW1100 made by DuPont) and 0.16 g of octafluoro-1,4-butanedisulfonamide were dissolved in 1.0 g of DMAc at room temperature. The solution was poured onto a glass plate and stood at room temperature for 40 minutes. The glass plate was moved to a vacuum oven and heated at 100° C. for hrs and 170° C. for 1.2 hrs. The film was peeled off and measured for in-plane conductivity at 120° C. and different relative humidity. The measurements are shown in Table 2.

TABLE 2

| Relative Humidity % | Conductivity mS/cm |
|---|---|
| 94.8 | 337 |
| 50 | 19.4 |
| 23.1 | 3.5 |
| 94.8 | 250 |

Example 4

A solution of 19.0 g of difluoro-fluorosulfonyl-acetyl fluoride (0.105 moles) in 250 mL toluene was prepared inside a glove box. A solution of 50 mL of 28% aqueous ammonia (0.73 moles) was diluted to 250 mL with deionized water and placed in a blender. The toluene solution was poured into the blender running at high speed. The ammonium fluoride was neutralized with 8.5 g of sodium hydroxide (0.21 moles). The aqueous phase was separated from the toluene, evaporated, and dried under vacuum. The residue was washed two times with a total of 500 mL of ethyl acetate. The extracts were dried with MgSO4, filtered, and evaporated to give 6.75 g. The solids were redissolved in 50 mL of ethyl acetate, filtered, and evaporated to give 5.61 g (28% crude yield) of the diamide adduct, 2,2-difluoro-2-sulfamoyl-acetamide, as shown by the following structure. $^{19}F$ NMR (DMSO-d6): −110.2 (s). MS (CI): m/z 174.999111 (M+H$^+$, 1.2 error), calcd. 174.998895 ($C_2H_4N_2O_3F2S+H^+$).

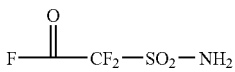

The 100 mL RBF containing 5.6 g of the diamide adduct (0.032 moles) was charged with 3.48 g of ortho-phenylene diamine (0.032 moles) and 40 mL of n-butanol. The mixture was heated to a reflux overnight under nitrogen. The white sublimate that formed in the condenser was discarded. The solvent was evaporated and the solids were dried under vacuum. The solids were recrystallized from water using decolorizing carbon. The white crystals of 2-(1H-benzoimidazol-2-yl)-2,2-difluoromethanesulfonamide, as shown by the following structure, weighed 3.05 g (38% yield). Melting point 248° C. $^1$H NMR (DMSO-d$_6$): 7.35 (m, 2H), 7.70 (m, 2H), 8.4 (bs, 2H), 13.4 (bs, 1H). $^{13}$C NMR (DMSO-d$_6$): 113.1 (C—H), 120.5 (C—H), 123.7 (2 C—H), 135.0 (C=C), 142.5 (C=C), 141.3 (t, $J_{CF}$=28 Hz, C—CF$_2$), 116.1 (t, $J_{CF}$=280 Hz, C—CF$_2$). $^{19}$F NMR (DMSO-d$_6$): −103.78 (s). MS (EI): m/z 247.0226 (M$^+$, 0.3 ppm error), calcd 247.0227 (C$_8$H$_7$F$_2$N$_3$O$_2$S).

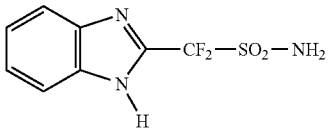

Example 5

A two-neck 200 mL round bottom flask equipped with a stirring bar, septum, and a Dewar-jacketed addition funnel with dry ice condenser was purged with nitrogen and charged with 100 mL of ether. Gaseous ammonia was condensed into the addition funnel until 14.6 mL (0.582 moles) was collected, then added to the ether cooled in dry ice. A two-neck 500 mL round bottom flask equipped with a stirring bar, dry ice condenser, and septum was purged with nitrogen and charged with 100 mL of ether. A solution of 26.4 g of difluorofluorosulfonyl-acetyl fluoride (0.146 moles) in 100 mL of ether was transferred to the flask by cannula and cooled to 0° C. using an ice bath. The solution of ammonia was slowly added by cannula and stirred for 1 hour. The reaction mixture was warmed to room temperature and stirred for 1 hour. The hygroscopic solids were filtered off under nitrogen, washed with ether, dried under vacuum, and stored under nitrogen in a glove box. The dry solids weighed 33.3 g for a 91% mass balance of a mixture of the ammonium cycloimidate, as shown by the following structure, and ammonium fluoride. $^{19}$F NMR (DMSO-d$_6$): −104.36 (s).

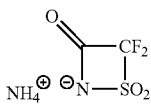

A 200 mL round bottom flask equipped with a stirring bar was charged with 12.41 g of the mixed salts (about 0.05 moles ammonium cycloimidate) inside a glove box. The flask was equipped with a reflux condenser and septum, then transferred to the hood and attached to a nitrogen bubbler. 16.22 g of ortho-phenylene diamine (0.15 moles) and 75 mL of n-butanol were added to the flask. The slurry was slowly heated to a reflux while purging the atmosphere to flush ammonia from the flask, and then left at reflux overnight. The solvent was evaporated and the residue recrystallized from acetonitrile using decolorizing carbon and then from water. The dried solids weighed 2.33 g for a 19% yield of 2-(1H-benzoimidazol-2-yl)-2,2-difluoromethanesulfonamide.

Example 6

A pellet of 2-(1H-benzoimidazol-2-yl)-2,2-difluoromethanesulfonamide was prepared using a hand press for the preparation of infrared spectroscopy samples. The pellet was 320 micrometers thick as measured for through-plane conductivity. The fixture had a short impedance of 0.240 ohms. The sample was heated to 200° C. and then cooled in 25° C. steps to 75° C. to obtain the measurements shown in Table 3.

TABLE 3

| | Temperature, ° C. | | | | |
|---|---|---|---|---|---|
| | 200 | 175 | 150 | 125 | 75 |
| Conductivity, mS/cm | 9.0 | 22.1 | 15.6 | 7.5 | 7.1 |

Example 7

Difluoro-fluorosulfonyl-acetyl fluoride was distilled by vacuum transfer into a Schlenk tube, weighed to give 73.95 g (0.41 moles), and dissolved in 50 mL of ether. Inside a glove box, a 1 L two-neck round bottom flask equipped with a stirring bar, gas inlet, and septum was charged with 43.0 g of poly(4-vinylpyridine), 2% cross-linked (0.41 moles), and 150 mL of ether. The solution was transferred from the Schlenk tube to the round bottom flask by cannula and cooled to 0° C. A solution of 6.56 g of hydrazine (0.20 moles) in 300 mL of ether was prepared inside a glove box and slowly added to the round bottom flask by cannula. The mixture was stirred for 1 hour, and then warmed to room temperature. The solids were filtered off and washed with ether. The filtrate was concentrated, transferred to a 100 mL round bottom flask, evaporated, and the solids dried under vacuum to give 60.4 g of N,N'-bis(2,2-difluoro-2-fluorosulfonyl-acetyl)hydrazine, as shown by the following structure, for an 86% crude yield.

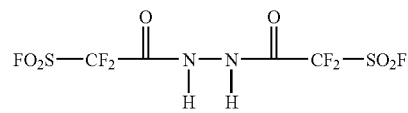

A stirring bar and 15 mL of 67.6% oleum (0.25 moles) was added to the flask, which was equipped with a micro-distillation apparatus. A clear liquid was vacuum distilled from the mixture at 92.5-114° C. and 37 Torr at a pot temperature of 120-150° C. The fuming liquid was washed with deionized water to remove residual oleum and the heavy liquid drained into a 100 mL round bottom flask. Sufficient phosphorus pentoxide was added to dry the liquid, which was redistilled at 92.5° C. and 37 Torr to give 42.1 g of 2,5-bis(difluorofluorosulfonyl-methyl)-[1,3,4]oxadiazole, as shown by the following structure, for an 62% pure yield. $^{19}$F NMR (CD$_3$CN): −99.93 (d, J=5.3 Hz, CF$_2$), 39.08 (t, J=5.3 Hz, SO$_2$F).

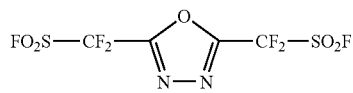

A 250 mL two-neck round bottom flask equipped with a stirring bar, septum, and dry ice condenser was purged with nitrogen, and then cooled to −78° C. Ammonia was condensed into the flask to collect about 20 mL. Inside a glove box, a 125 mL flask was charged with 3.342 g of 2-5-bis(difluoro-fluorosulfonyl-methyl)-[1,3,4]oxadiazole (0.010 moles), 100 mL of acetonitrile, and sealed with a septum. The solution was added to the ammonia at −33° C. by cannula under nitrogen. The solution was stirred overnight under nitrogen. The mixture was treated with 55 mL of 2M hydrogen chloride in ether and 1.5 g of calcium chloride (0.014 moles). The solids that precipitated were filtered off and washed with acetonitrile. The solvents were evaporated and the residue was dried under vacuum to give 3.07 g for a 94% crude yield. The mixture was subjected to chromatography on silica gel using ethyl acetate and hexane. The common fractions were evaporated to give 0.80 g of bis(difluoro-sulfamoyl-methyl)-[1,3,4]oxadiazole, as shown by the following structure, for a 24% yield. Melting point: 171-172° C. $^{19}$F NMR (CD$_3$CN): −106.64 (s, CF$_2$). MS (CI): m/z 328.963722 (M+H$^+$, 0.1 ppm error), calculated 328.963751 (C$_4$H$_4$N$_4$O$_5$F$_4$S$_2$+H$^+$).

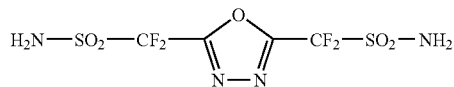

Example 8

A glass tube was charged with 1.098 g of bis(difluoro-sulfamoyl-methyl)-[1,3,4]oxadiazole and analyzed for liquid conductivity. The tube was first heated to 180° C. to melt the sample. The tube was then heated to 220° C. and cooled to 140° C. in 10° C. steps to obtain the measurements shown in Table 4. The sample lost 0.041 g on the first cycle.

For the second cycle, 0.117 g water was added to the cooled tube to give a sample containing 10 weight % water. The tube was heated to 170° C. to remelt the sample, and then heated to 220° C. and cooled to 170° C. in 10° C. steps to obtain the measurements shown in Table 4. The sample lost 0.119 g on the second cycle, which corresponded closely to the amount of water added before the second cycle.

TABLE 4

| | Temperature, ° C. | | | | | |
|---|---|---|---|---|---|---|
| | 170 | 180 | 190 | 200 | 210 | 220 |
| Conductivity (1$^{st}$ heat), mS/cm | — | 0.18 | 0.24 | 0.32 | 0.42 | 0.37 |
| Conductivity (1$^{st}$ cool), mS/cm | 0.37 | 0.47 | 0.53 | 0.47 | 0.45 | — |
| Conductivity (2$^{nd}$ heat), mS/cm | 0.26 | 0.46 | 0.58 | 0.60 | 0.67 | 0.47 |
| Conductivity (2$^{nd}$ cool), mS/cm | 0.28 | 0.29 | 0.33 | 0.31 | 0.37 | — |

Example 9

A sample of 2-(1H-benzoimidazol-2-yl)-2,2-difluoromethanesulfonamide was freshly recrystallized from acetonitrile. The undried crystals were used to prepare pellets using a hand press for the preparation of infrared spectroscopy samples. The fixture had a short impedance of 0.311 ohms. The first pellet was treated with a drop of deionized water and was 470 micrometers thick as measured for through-plane conductivity. The second pellet was 580 micrometers thick as measured dry for through-plane conductivity. The samples were heated in 25° C. steps to obtain the measurements shown in Table 5.

TABLE 5

| | Temperature, ° C. | | | | |
|---|---|---|---|---|---|
| | 100 | 125 | 150 | 175 | 200 |
| Conductivity (wet), mS/cm | 0.41 | 0.45 | 0.39 | — | — |
| Conductivity (dry), mS/cm | — | — | — | 0.12 | 0.16 |

What is claimed is:

1. A fluorinated sulfonamide small molecule having the general structure:

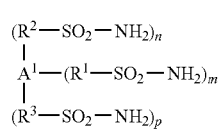

wherein m, n and p are 0 to 3, with the proviso that m+n+p is equal to 1 to 4;

A$^1$ is an aromatic heterocyclic group, with the proviso that carbon atoms of the heterocyclic ring are fully substituted by fluorinated sulfonamide groups; and R$^1$, R$^2$, and R$^3$ are linear or branched perfluoroalkylene groups, optionally containing oxygen, chlorine, bromine, or iodine atoms.

2. The fluorinated sulfonamide small molecule of claim 1 wherein m, n and p are 0 to 2, with the proviso that m+n+p is equal to 1 to 2.

3. The fluorinated sulfonamide small molecule of claim 1 wherein the aromatic heterocyclic group is selected from the group consisting of benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, tetrazole, pyrazole, triazole, oxadiazole, and thiadiazole.

4. The fluorinated sulfonamide small molecule of claim 3 wherein the aromatic heterocyclic group is selected from the group consisting of benzimidazole, benzoxazole, benzothiazole, and triazine.

5. The fluorinated sulfonamide small molecule of claim 1 wherein the aromatic heterocyclic group is benzimidazole.

6. The fluorinated sulfonamide small molecule of claim 1 wherein the linear or branched perfluoroalkylene groups, optionally containing oxygen, chlorine, bromine, or iodine atoms contain 1 to 20 carbon atoms.

7. The fluorinated sulfonamide small molecule of claim 6 wherein R$^1$, R$^2$, and R$^3$ are linear perfluoroalkylene groups containing 1 to 6 carbon atoms.

8. A polymerizable perfluorinated or partially fluorinated trifluorovinyl monomer comprising aromatic heterocyclic groups substituted by fluorinated sulfonamide groups and having the general structure:

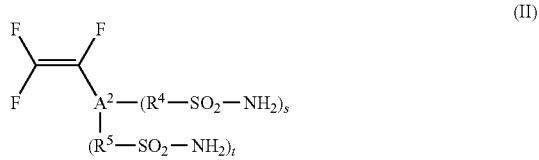

(II)

wherein s and t are the number of fluorinated sulfonamide groups attached to the heterocyclic ring and are equal 0 to 2, with the proviso that s+t is equal to 1 to 2;
$A^2$ is an aromatic heterocyclic group, with the proviso that carbon atoms of the heterocyclic ring are fully substituted by either the trifluorovinyl group or the fluorinated sulfonamide groups; and
$R^4$ and $R^5$ are linear or branched perfluoroalkylene groups, optionally containing oxygen, chlorine, bromine, or iodine atoms.

9. The polymerizable perfluorinated or partially fluorinated trifluorovinyl monomer of claim 8 wherein the aromatic heterocyclic group selected from the group consisting of benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, pyrazole, triazole, oxadiazole, and thiadiazole.

10. The polymerizable perfluorinated or partially fluorinated trifluorovinyl monomer of claim 8 wherein $R^4$ and $R^5$ are linear perfluoroalkylene groups containing 1 to 6 carbon atoms.

11. A fluorinated sulfonamide vinyl polymer having the general structure:

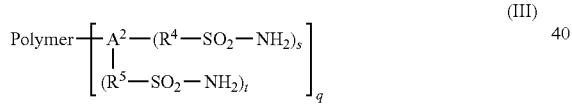

(III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

12. The fluorinated sulfonamide vinyl polymer of claim 11 wherein the aromatic side chain group is phenyl.

13. The fluorinated sulfonamide vinyl polymer of claim 11 wherein Polymer is selected from the group consisting of polytetrafluoroethylene, polytrifluorostyrene, and polychlorotrifluoroethylene.

14. The fluorinated sulfonamide vinyl polymer of claim 11 wherein q is 0.1 to 1.

15. The fluorinated sulfonamide vinyl polymer of claim 14 wherein q is 0.6 to 1.

16. The fluorinated sulfonamide vinyl polymer of claim 11 wherein the aromatic heterocyclic group is selected from the group consisting of benzimidazole, benzoxazole, benzothiazole, benzobisimidazole, benzobisoxazole, benzobisthiazole, bibenzimidazole, bibenzoxazole, bibenzothiazole, imidazole, oxazole, thiazole, triazine, pyrazole, triazole, oxadiazole, and thiadiazole.

17. The fluorinated sulfonamide vinyl polymer of claim 16 wherein the aromatic heterocyclic group is selected from the group consisting of benzimidazole, benzoxazole, benzothiazole, and triazine.

18. The fluorinated sulfonamide vinyl polymer of claim 17 wherein the aromatic heterocyclic group is benzimidazole.

19. The fluorinated sulfonamide vinyl polymer of claim 11 wherein the linear or branched perfluoroalkylene group, optionally containing oxygen, chlorine, bromine, or iodine atoms, contains 1 to 20 carbon atoms.

20. The fluorinated sulfonamide vinyl polymer of claim 17 wherein $R^4$ and $R^5$ are linear perfluoroalkylene groups containing 1 to 6 carbon atoms.

21. A polymer electrolyte membrane comprising a compound having fluorinated sulfonamide groups, —$CF_2$—$SO_2$—$NH_2$, selected from the group consisting of:
(a) a small molecule having general structure:

(I)

wherein m, n and p are 0 to 3, with the proviso that m+n+p is equal to 1 to 4;
$A^1$ is an aromatic heterocyclic group, with the proviso that carbon atoms of the heterocyclic ring are fully substituted by fluorinated sulfonamide groups; and
$R^1$, $R^2$, and $R^3$ are linear or branched perfluoroalkylene groups, optionally containing oxygen, chlorine, bromine, or iodine atoms; and
(b) a polymer having general structure:

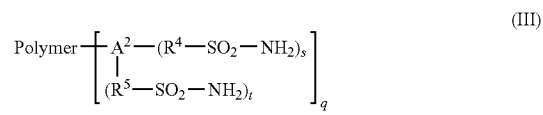

(III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

22. The polymer electrolyte membrane of claim 21 wherein compound is a small molecule.

23. The polymer electrolyte membrane of claim 21 wherein compound is a polymer.

24. The polymer electrolyte membrane of claim 21 further comprising supporting materials.

25. A membrane electrode assembly comprising a polymer electrolyte membrane, wherein the polymer electrolyte membrane has a first surface and a second surface, and comprises a compound having fluorinated sulfonamide groups, —$CF_2$—$SO_2$—$NH_2$, selected from the group consisting of:
(a) a small molecule having general structure:

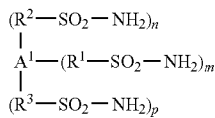
(I)

wherein m, n and p are 0 to 3, with the proviso that m+n+p is equal to 1 to 4;

$A^1$ is an aromatic heterocyclic group, with the proviso that carbon atoms of the heterocyclic ring are fully substituted by fluorinated sulfonamide groups; and $R^1$, $R^2$, and $R^3$ are linear or branched perfluoroalkylene groups, optionally containing oxygen, chlorine, bromine, or iodine atoms; and (b) a polymer having general structure:

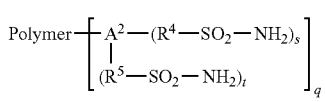
(III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

26. The membrane electrode assembly of claim 25 further comprising at least one electrode prepared from an electrocatalyst coating composition present on the first or second surfaces of the membrane.

27. An membrane electrode assembly of claim 26 wherein the electrocatalyst composition comprises a polymer having the general structure:

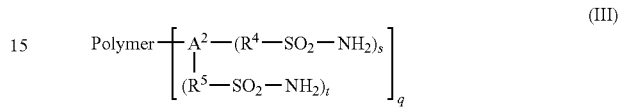
(III)

wherein Polymer is a polyperfluorocarbon or polypartially fluorinated carbon vinyl polymer backbone optionally containing aromatic side chain groups; q is the mole fraction of fluorinated sulfonamide side chain groups and is selected from 0.01 to 1; s and t are the number of fluorinated sulfonamide groups attached to the heterocyclic ring and are equal 0 to 2, with the proviso that s+t is equal to 1 to 2; $A^2$ is an aromatic heterocyclic group, with the proviso that the carbon atoms of the heterocyclic ring are fully substituted by the polymer backbone or the fluorinated sulfonamide groups; and $R^4$ and $R^5$ are linear or branched perfluoroalkylene groups, optionally containing oxygen, chlorine, bromine, or iodine atoms.

28. The membrane electrode assembly of claim 27 wherein the electrocatalyst composition further comprises a catalyst.

29. An electrochemical cell comprising the membrane electrode assembly according to claim 25.

30. An electrocatalyst composition comprising a polymer according to claim 11.

31. The electrocatalyst composition of claim 30 further comprising a catalyst.

* * * * *

UNITED STATES PATENT AND TRADEMARK OFFICE
CERTIFICATE OF CORRECTION

PATENT NO. : 7,659,026 B2 Page 1 of 1
APPLICATION NO. : 10/560882
DATED : February 9, 2010
INVENTOR(S) : Mark F. Teasley It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1084 days.

Signed and Sealed this

Twenty-eighth Day of December, 2010

David J. Kappos
*Director of the United States Patent and Trademark Office*